US009546971B2

United States Patent
Kinoshita

(10) Patent No.: US 9,546,971 B2
(45) Date of Patent: Jan. 17, 2017

(54) DIAGNOSIS DEVICE FOR TEMPERATURE SENSOR

(71) Applicant: Fuji Jukogyo Kabushiki Kaisha, Tokyo (JP)

(72) Inventor: Takahiro Kinoshita, Tokyo (JP)

(73) Assignee: FUJI JUKOGYO KABUSHIKI KAISHA, Tokyo (JP)

(*) Notice: Subject to any disclaimer, the term of this patent is extended or adjusted under 35 U.S.C. 154(b) by 340 days.

(21) Appl. No.: 14/271,310

(22) Filed: May 6, 2014

(65) Prior Publication Data

US 2014/0341249 A1    Nov. 20, 2014

(30) Foreign Application Priority Data

May 16, 2013  (JP) ................................. 2013-104058

(51) Int. Cl.
*G01N 25/72* (2006.01)
*G01K 7/22* (2006.01)
(Continued)

(52) U.S. Cl.
CPC .............. *G01N 25/72* (2013.01); *F16H 59/72* (2013.01); *G01K 7/22* (2013.01); *G01K 15/007* (2013.01);
(Continued)

(58) Field of Classification Search
CPC ............ G01N 25/72; G01K 1/00; G01K 7/22; G01K 15/007; G01K 2013/026; G01K 2205/00; F16H 59/72; F16H 2061/1284; F16H 2061/1208
(Continued)

(56) References Cited

U.S. PATENT DOCUMENTS 5,107,246 A * 4/1992 Mogaki .................. F16H 61/12
340/449
5,995,887 A * 11/1999 Hathaway .............. G01K 15/00
340/449
(Continued)

FOREIGN PATENT DOCUMENTS

DE        10221992 C1    11/2003
JP     2000-282930 A    10/2000
(Continued)

OTHER PUBLICATIONS

JPO Decision to Grant a Patent dated Jan. 6, 2015.
English Translation of German Office Action dated Jun. 27, 2016.

*Primary Examiner* — Lisa Caputo
*Assistant Examiner* — Philip Cotey
(74) *Attorney, Agent, or Firm* — McGinn IP Law Group, PLLC.

(57) ABSTRACT

A diagnosis device for a temperature sensor provided to a power transmission device transmits driving force generated by a driving power source of a vehicle. The diagnosis device includes: an output voltage estimating unit to calculate an output voltage estimation value of the temperature sensor, based on the operating state of the vehicle; and an output voltage stuck malfunction determining unit to determine an output voltage stuck malfunction of the temperature sensor, in a case where the amount of change of the output voltage estimation value is equal to or above a first threshold value, and the amount of change of output voltage of the temperature sensor is equal to or below a second threshold value.

6 Claims, 2 Drawing Sheets

(51) Int. Cl.
   *G01K 15/00*    (2006.01)
   *F16H 59/72*    (2006.01)
   *F16H 61/12*    (2010.01)
   *G01K 13/02*    (2006.01)

(52) U.S. Cl.
   CPC .................. *F16H 2061/1208* (2013.01); *F16H 2061/1284* (2013.01); *G01K 2013/026* (2013.01); *G01K 2205/00* (2013.01)

(58) Field of Classification Search
   USPC .............................................. 374/4, E15.001
   See application file for complete search history.

(56) References Cited

U.S. PATENT DOCUMENTS

| | | | | |
|---|---|---|---|---|
| 8,197,131 | B2* | 6/2012 | Kitajima | F16H 61/12 374/141 |
| 2002/0046618 | A1* | 4/2002 | Yamashita | F16H 59/72 74/335 |
| 2006/0149441 | A1* | 7/2006 | Takamura | G01K 15/00 701/29.2 |
| 2006/0241841 | A1* | 10/2006 | Brunstetter | G01K 15/007 701/63 |
| 2007/0030068 | A1* | 2/2007 | Motonobu | F16H 61/12 330/257 |
| 2008/0253429 | A1* | 10/2008 | Choi | F16H 61/12 374/144 |
| 2009/0168832 | A1* | 7/2009 | Bauerle | F02D 41/222 374/1 |
| 2010/0195693 | A1* | 8/2010 | Kitajima | F16H 61/12 374/1 |
| 2011/0054759 | A1 | 3/2011 | Eser | |

FOREIGN PATENT DOCUMENTS

| | | |
|---|---|---|
| JP | 2004-011869 A | 1/2004 |
| JP | 2004-90683 A | 3/2004 |
| JP | 2004-325110 A | 11/2004 |
| JP | 2008-107089 A | 5/2008 |
| WO | WO 2009/089978 A1 | 7/2009 |

* cited by examiner

DIAGNOSIS DEVICE FOR TEMPERATURE SENSOR

CROSS-REFERENCES TO RELATED APPLICATIONS

The present application claims priority from Japanese Patent Application No. 2013-104058 filed on May 16, 2013, the entire contents of which are hereby incorporated by reference.

BACKGROUND

1. Technical Field

The present invention relates to a diagnosis device for a temperature sensor provided to an automobile transmission or the like, for example, and more particularly relates to suitably detecting an output voltage stuck (seized) malfunction of a temperature sensor.

2. Related Art

Automatic transmissions in automobiles, for example, have a temperature sensor to detect the temperature of automatic transmission fluid (ATF). ATF serves both as a hydraulic operating fluid and a lubricant. In a case where such a sensor malfunctions, control of the automatic transmission may encounter problems. Accordingly, various types of malfunction diagnosis techniques have been conventionally proposed.

For example, according to a technique described Japanese Unexamined Patent Application Publication (JP-A) No. 2004-11869 the detection value of the external air surrounding the automobile and the detection value of an fluid temperature sensor are compared. If the detection value of the fluid temperature is lower than the external air, the fluid temperature sensor is determined to be malfunctioning. Also, JP-A No. 2008-107089 describes a technique to diagnose a state in which temperature drifting of a thermocouple temperature sensor is occurring. Usage time at a temperature at which temperature drifting is apt to occur is weighted in accordance with the temperature, and the state of occurrence of temperature drifting is diagnosed based on an amount of drift estimated from an added value of weighted usage time.

An output voltage stuck malfunction may occur in an temperature sensor such as described above, where the output voltage sticks (seizes) at a certain output voltage. One technique for this is that an operating state where temperature change occurs is distinguished using accumulated running time, and malfunction is determined in a case where the output voltage of the temperature sensor is substantially unchanged over a predetermined amount of time. However, this technique may lead to erroneous diagnosis in cases such as where the amount of heat generated and the amount of cooling due to wind from driving are balanced, and the actual temperature of the object of measurement (e.g., ATF) is substantially constant.

SUMMARY OF THE INVENTION

It is an object of the present invention to provide a diagnosis device for a temperature sensor, to suitably detect an output voltage stuck (seized) malfunction of the temperature sensor.

An aspect of the present invention provides a diagnosis device for a temperature sensor provided to a power transmission device that transmits driving force generated by a driving power source of a vehicle. The diagnosis device includes: an output voltage estimating unit to calculate an output voltage estimation value of the temperature sensor, based on the operating state of the vehicle; and an output voltage stuck malfunction determining unit to determine an output voltage stuck malfunction of the temperature sensor, in a case where the amount of change of the output voltage estimation value is equal to or above a first threshold value, and the amount of change of output voltage of the temperature sensor is equal to or below a second threshold value.

The output voltage stuck malfunction determining unit may determine the output voltage stuck malfunction, in a case where the amount of change of the output voltage estimation value is equal to or above a first threshold value and the amount of change of output voltage of the temperature sensor is equal to or below a second threshold value, and this state continues for a predetermined amount of time or longer.

The output voltage estimating unit may calculates an output voltage estimation value for each of a hot external air state and a cold external air state, and the output voltage stuck malfunction determining unit may determine the output voltage stuck malfunction only in a case where the output voltage estimation value is equal to or above the first threshold value in both the hot external air state and a cold external air state.

DETAILED DESCRIPTION

The present invention solves the object to provide a diagnosis device for a temperature sensor to suitably detect an output voltage stuck malfunction of the temperature sensor as follows. Estimated values of temperature sensor output voltage according to a running state of a vehicle are calculated at two standards, one of which is when external air is hot, and the other when external air is cold. If both of these exhibit change of a predetermined value or greater, but the output voltage of the temperature sensor is substantially unchanged for a continued time, determination is made that the temperature sensor is malfunctioning.

Now, an implementation of a diagnosis device for a temperature sensor, to which the present invention has been applied, will be described. The diagnosis device for a temperature sensor according to the implementation diagnoses output voltage stuck malfunctions of an automatic transmission fluid temperature sensor in an automobile or the like, for example.

Figure 1:
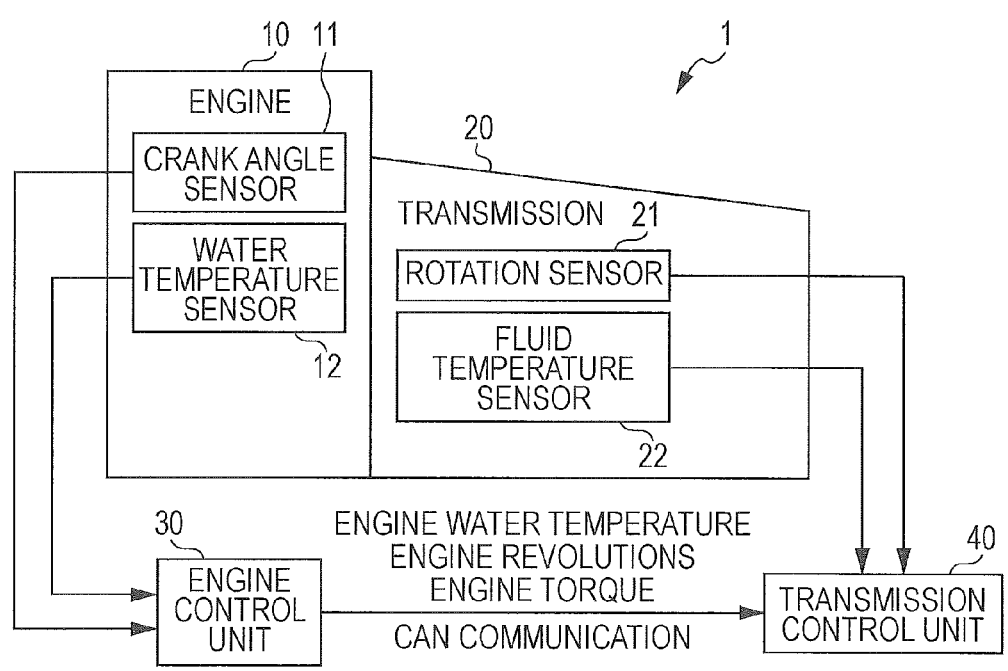
FIG. 1 is a schematic diagram illustrating the configuration of a power train of a vehicle, to which a diagnosis device for a temperature sensor, according to an implementation of the present invention, has been applied.

FIG. 1 is a schematic diagram illustrating the configuration of a power train of a vehicle, to which the diagnosis device for a temperature sensor according to the implementation has been applied. The power train 1 is configured including an engine 10, a transmission 20, an engine control unit 30, a transmission control unit 40, and so forth, as illustrated in FIG. 1.

The engine is an internal combustion engine such as a four-stroke gasoline or diesel engine, used as a driving power source of a vehicle. The engine 10 includes various sensors, such as a crank angle sensor 11, water temperature sensor 12, and so forth.

The crank angle sensor 11 successively detects the rotational position of the crank shaft, which is the output shaft of the engine 10. The output of the crank angle sensor 11 is transmitted to the engine control unit 30. The engine control unit 30 is capable of detecting rotational speed of the crank shaft based on the output from the crank angle sensor 11. The water temperature sensor 12 is a temperature sensor which detects the temperature of the coolant water of the engine 10.

The transmission 20 reduces or increases the rotational output of the crankshaft from the engine 10, so as to transmit driving force to the fore and aft axle differentials via an all-wheel-drive (AWD) transfer case. The transmission 20 is a chain-driven Continuously Variable Transmission (CVT) having a variator where a chain runs between a pair of pulleys.

The transmission 20 is provided with various types of sensors, such as a rotation sensor 21, fluid temperature sensor 22, and so forth. The rotation sensor 21 is a group of multiple sensors which detect the rotational speed of primary parts, such as the input and output shafts of the transmission 20, and so forth. The fluid temperature sensor 22 is a sensor which detects the temperature of CVT fluid (ATF) serving both as a hydraulic operating fluid and a lubricant, i.e., an ATF temperature sensor, and includes a thermistor.

The engine control unit 30 centrally controls the engine 10 and the auxiliaries thereof. The engine control unit 30 is configured including an information processing device such as a central processing unit (CPU) or the like, storage devices such as random access memory (RAM), read-only memory (ROM), and so forth, an input/output interface, a bus connecting these members, and so forth. The engine control unit 30 also uses an onboard local area network (LAN) device such as a controller area network (CAN) communication system or the like to transmit various types of information to the transmission control unit 40, such as coolant temperature of the engine 10, rotational speed of the crankshaft, output torque, and so forth.

The transmission control unit 40 centrally controls the transmission 20 and the auxiliaries thereof. The transmission control unit 40 is configured including an information processing device such as a central processing unit (CPU) or the like, storage devices such as random access memory (RAM), read-only memory (ROM), and so forth, an input/output interface, a bus connecting these members, and so forth. The transmission control unit 40 performs gearshift control, lock-up control, control of engaging force of the AWD transfer clutch, and so forth, of the transmission 20.

The transmission control unit 40 also functions as the malfunction diagnosis device to diagnose an output voltage stuck malfunction where the output voltage of the fluid temperature sensor 22 sticks at a certain value. The transmission control unit 40 serves as the output voltage estimating unit to estimate an output voltage estimation value of the fluid temperature sensor 22 based on the operating state of the vehicle, and the output voltage stuck malfunction determining unit to determine an output voltage stuck malfunction by comparing the output voltage estimation value with the output voltage of the fluid temperature sensor 22.

Note that the diagnosis which will be described below is not executed in cases where the output voltage of the fluid temperature sensor 22 has deviated from a normal range set beforehand, in cases where an error has occurred in a communication system such as the CAN communication system or the like, or at any of the electrical control units (ECU), in cases where the water temperature sensor 12 is malfunctioning, causes where an engine malfunction warning is being output, and so forth.

Figure 2:
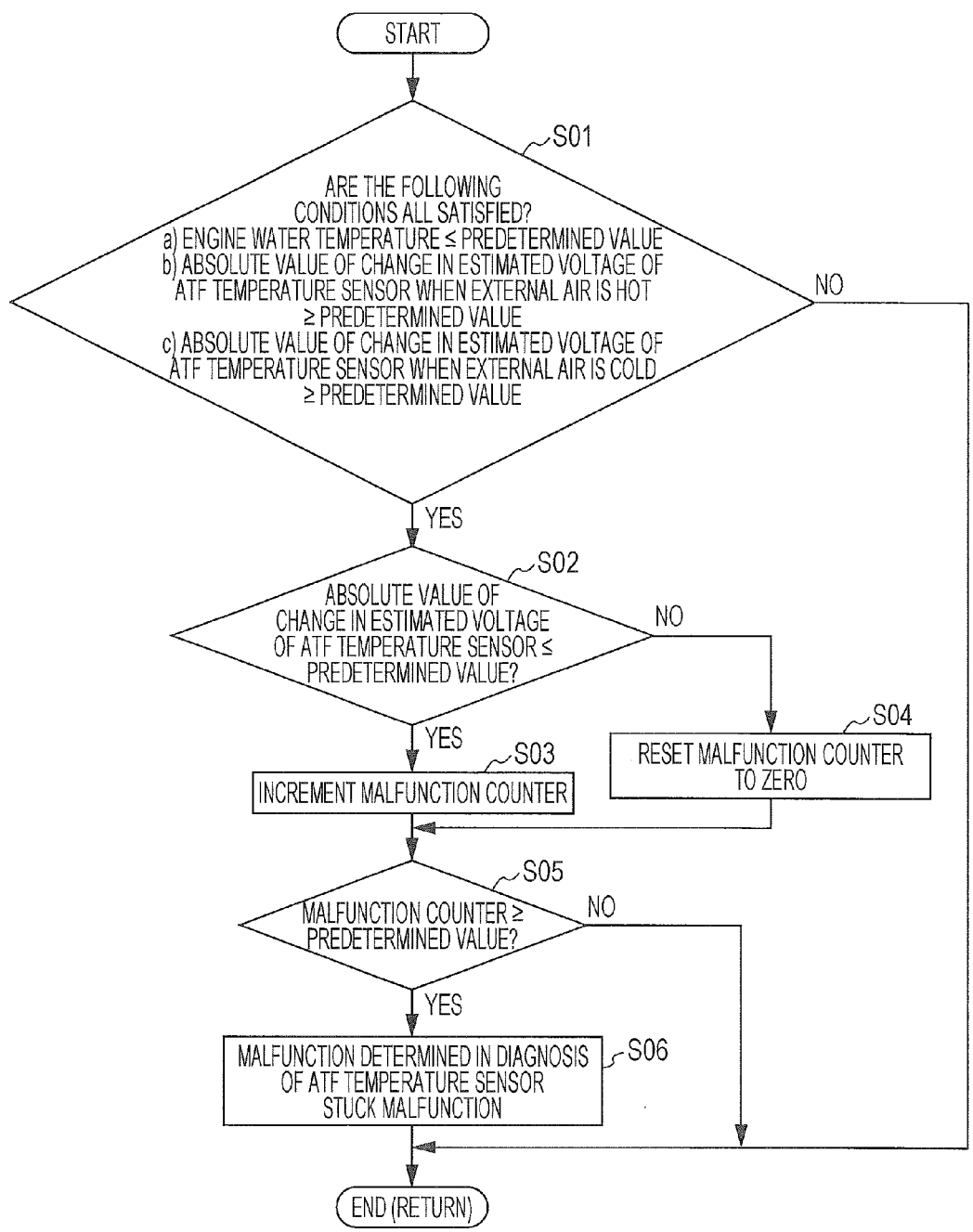
FIG. 2 is a flowchart illustrating a method of diagnosing an output voltage stuck malfunction by the diagnosis device for a temperature sensor according to the implementation.

This malfunction diagnosis function will now be described in detail. FIG. 2 is a flowchart illustrating a method of diagnosing an output voltage stuck malfunction by the diagnosis device for a temperature sensor according to the implementation, which will be described following the individual steps.

Step S01: Judging Conditions to Execute Diagnosis

The transmission control unit 40 distinguishes whether or not all of the following conditions a) through c) have been satisfied, and if all are satisfied, the flow advances to step S02. If any one is not satisfied, the flow ends (returns).

a) engine water temperature≤predetermined value (e.g., 80° C.)

b) absolute value of change in estimated voltage of ATF temperature sensor (fluid temperature sensor) when external air is hot≥predetermined value (e.g., 0.05 V/min)

c) absolute value of change in estimated voltage of ATF temperature sensor (fluid temperature sensor) when external air is cold≥predetermined value (e.g., 0.05 V/min)

A method for calculating the absolute value of change in estimated voltage of ATF temperature sensor when external air is hot or cold will be described in detail later.

Step S02: Judging Absolute Value of Change in Voltage of ATF Temperature Sensor

The transmission control unit 40 compares the absolute value of change in output voltage of the fluid temperature sensor 22 (absolute value of change in voltage of fluid temperature sensor) with a predetermined value that has been set beforehand (e.g., 0.025 V/min). If not greater than the predetermined value, the flow advances to step S03, and otherwise advances to step S04. A calculation method of the absolute value of change in voltage of fluid temperature sensor will be described in detail later.

Step S03: Increment Malfunction Counter

The transmission control unit 40 increments the counter value of a malfunction counter which counts the duration of time where the absolute value of change in voltage of the ATF temperature sensor is in a state of being not greater than the predetermined value in step S02. The flow subsequently advances to step S05.

Step S04: Reset Malfunction Counter to Zero

The transmission control unit 40 resets the counter value of the malfunction counter to zero. The flow subsequently advances to step S05.

Step S05: Judging Malfunction Counter Value

The transmission control unit 40 compares the counter value of the malfunction counter with a predetermined value that has been set beforehand (a value equivalent to 60 seconds, for example).

If the counter value of the malfunction counter is equal to or greater than the predetermined value, the flow advances to step S06. Otherwise, the flow ends (returns).

Step S06: ATF Temperature Sensor Stuck Malfunction Finalized

The transmission control unit 40 finalizes the determination for an output voltage stuck malfunction of the fluid temperature sensor 22, and ends the flow.

Next, how to calculate the parameters used in the above-described flowchart will be described in detail.

The absolute value of change in fluid temperature sensor voltage is obtained from Expression 1. This absolute value of change in fluid temperature sensor voltage is successively calculated every 10 msec, for example.

absolute value of change in fluid temperature sensor voltage (V/min)=|change in fluid temperature sensor voltage|(V/min)  (Expression 1)

Change in fluid temperature sensor voltage is obtained from Expression 2.

change in fluid temperature sensor voltage V/min=fluid temperature sensor voltage $n$–fluid temperature sensor voltage $n-1$  (Expression 2)

The absolute value of change in estimated voltage of the fluid temperature sensor when the external air is hot is obtained from Expression 3. This absolute value of change in estimated voltage of the fluid temperature sensor when the external air is hot is successively calculated every 10 msec, for example.

absolute value of change in estimated voltage of fluid temperature sensor when external air is hot (V/min)=|change in estimated voltage of fluid temperature sensor when external air is hot|(V/min)  (Expression 3)

The change in estimated voltage of the fluid temperature sensor when external air is hot is obtained from Expression 4.

change in estimated voltage of fluid temperature sensor when external air is hot V/min=estimated voltage of fluid temperature sensor when external air is hot $n$–estimated voltage of fluid temperature sensor when external air is hot $n-1$  (Expression 4)

The estimated voltage of the fluid temperature sensor when external air is hot is obtained from Expression 5.

estimated voltage of fluid temperature sensor when external air is hot V=fluid temperature sensor voltage conversion table value (estimated value of ATF temperature sensor when external air is hot) V  (Expression 5)

The absolute value of change in estimated voltage of the fluid temperature sensor when the external air is cold is obtained from Expression 6. This absolute value of change in estimated voltage of the fluid temperature sensor when the external air is cold is successively calculated every 10 msec, for example.

absolute value of change in estimated voltage of fluid temperature sensor when external air is cold (V/min)=|change in estimated voltage of fluid temperature sensor when external air is cold|(V/min)  (Expression 6)

The change in estimated voltage of the fluid temperature sensor when external air is cold is obtained from Expression 7.

change in estimated voltage of fluid temperature sensor when external air is cold V/min=estimated voltage of fluid temperature sensor when external air is cold $n$–estimated voltage of fluid temperature sensor when external air is cold $n-1$  (Expression 7)

The estimated voltage of the fluid temperature sensor when external air is cold is obtained from Expression 8.

estimated voltage of fluid temperature sensor when external air is cold V=fluid temperature sensor voltage conversion table value (estimated value of ATF temperature sensor when external air is cold) V  (Expression 8)

The estimated value of the ATF temperature sensor when external air is hot is successively calculated every 10 msec, for example. This estimated value of the ATF temperature sensor when external air is hot is an estimated value calculated based on the running state history of the vehicle under a high-temperature environment (e.g., external temperature 40° C.)

Note that the estimated value of the ATF temperature sensor when external air is cold is calculated in essentially the same way as with the estimated value of the ATF temperature sensor when external air is hot, except that the external air temperature is changed from 40° C. to −40° C. This estimated value of the ATF temperature sensor when external air is cold is an estimated value calculated based on the running state history of the vehicle under a cold-temperature environment (e.g., external temperature −40° C.)

First, when the conditions of starting-up determination are satisfied, the estimated value of the ATF temperature sensor when external air is hot is obtained from Expression 9.

estimated value of the ATF temperature sensor when external air is hot ° C.=ATF temperature ° C.  (Expression 9)

When the conditions of starting-up determination are not satisfied, the estimated value of the ATF temperature sensor when external air is hot is obtained from Expression 10.

estimated value of the ATF temperature sensor when external air is hot ° C.=cumulative value of engine heat generation (high temperature)(kW)× heat-quantity/temperature conversion coefficient (high temperature)  (Expression 10)

Note that the heat-quantity/temperature conversion coefficient (high temperature) here is 0.005° C./kW, for example.

The conditions of starting-up determination are satisfied when the ignition switch is turned from off to on, and is no longer satisfied when a state of engine revolutions of 500 rpm or higher continues for one second or more. Otherwise, previous determination results are held.

The cumulative value of engine heat generation (high temperature) is obtained from Expression 11.

cumulative value of engine heat generation (high temperature) $n$ (kW)=cumulative value of engine heat generation (high temperature) $n-1$ (kW)+engine heat generation (high temperature) (kW/s)×0.01  Expression 11)

The engine heat generation (high temperature) is obtained from Expression 12.

engine heat generation (high temperature)(kW/s) =engine power loss (kW/s)+ATF warmer heat generation (high temperature)(kW/s)−heat cooled by wind (high temperature) (kW/s)  (Expression 12)

The ATF warmer heat generation (high temperature) is obtained from Expression 13.

ATF warmer heat generation (high temperature) =ATF warmer heat generation table value (ATF warmer flow rate)(kW/s)×engine water temperature (° C.)−estimated value of ATF temperature when external air is hot $n-1$/(fluid temperature at time of evaluating ATF warmer properties (° C.)−engine water temperature at time of evaluating ATF warmer properties (° C.))×ATF warmer heat generation (high temperature) correction coefficient (1.0)  (Expression 13)

The ATF warmer flow rate is obtained from Expression 14.

ATF warmer flow rate (L/min)=ATF warmer flow rate table value (engine rotation speed)  (Expression 14)

The following parameters are set based on an AFT warmer properties table.

ATF warmer heat generation table value (ATF warmer flow rate)

ATF Flow Rate Table Value

Fluid temperature at time of evaluating ATF properties (e.g., 120° C.)

Engine water temperature at time of evaluating ATF properties (e.g., 80° C.)

The heat cooled by wind (high temperature) is calculated from Expression 15.

heat cooled by wind (high temperature)(kW/s)=vehicle speed (km/h)×1000 (m/Km)/60 (min/h)/60 (min/s)×opening area (m$^2$)×specific heat of air (J/kg/K)×air density (kg/m$^3$)×estimated value of ATF temperature when external air is hot $n-1$ (° C.)−external air temperature when external air is hot (° C.)×heat cooled by wind (high temperature) correction coefficient/1000   (Expression 15)

The parameters are set as follows.
Specific heat of air=1030 (J/kg/K) (at humidity 100%)
Air density=1.293 kg/m$^2$) (at 0° C., 1 atm)
External air temperature when external air is hot=40° C.
Opening area=1.0 (m$^2$)
Heat cooled by wind (high temperature) correction coefficient=0.025

Note that the heat cooled by wind (low temperature) correction coefficient used for calculating the estimated value of ATF temperature when external air is cold is, for example, 0.0101

The engine power loss is obtained from Expression 16.

engine power loss (kW/s)=horsepower generated by engine (kW/s)−traveling resistance power (kW/s)   (Expression 16)

The lower value of the engine power loss is limited so as to be no lower than 0.

The horsepower generated by the engine is obtained from Expression 17.

horsepower generated by engine (kW/s)=engine torque (N·m)×engine revolutions (rpm)×2π/60 (s/min)/1000   (Expression 17)

Further, deviation in the estimated value of torque of the engine which during warm-up is corrected based on torque converter properties, using Expression 18.

engine torque (N·m)≤estimated value of torque of engine from torque converter properties (N·m)   (Expression 18)

The estimated value of torque of the engine from torque converter properties is obtained from Expression 19.

estimated value of torque of engine from torque converter properties (N·m)=engine revolutions (rpm)$^2$×torque converter capacity coefficient (speed ratio of torque converter)(N·m/rpm$^2$)   (Expression 19)

The speed ratio of the torque converter is obtained from Expression 20.

torque converter speed ratio=output revolutions (rpm)/input revolutions (rpm)   (Expression 20)

The traveling resistance power is obtained from Expression 21.

traveling resistance power (kW/s)=inertia-and-acceleration resistance power (kW/s)+air resistance power (kW/s)+rolling resistance power (kW/s)   (Expression 21)

The inertia-and-acceleration resistance power is obtained from Expression 22.

inertia-and-acceleration resistance power (kW/s)=inertia resistance power (kW/s)+acceleration resistance power (kW/s)   (Expression 22)

The inertia resistance power is obtained from Expression 23.

inertia resistance power (kW/s)=engine inertia resistance power (kW/s)+primary pulley inertia resistance power (kW/s)   (Expression 23)

The engine inertia resistance power is obtained from Expression 24.

engine inertia resistance power (kW/s)=engine inertia resistance (N·m)×engine revolutions (rpm)×2π/60 (s/min)/1000   (Expression 24)

The engine inertia resistance is obtained from Expression 25.

engine inertia resistance (N·m)=engine revolutions (rpm/s)×2π/60 (s/min)×engine inertia resistance coefficient (kg·m·s$^2$)×9.8 (m/s$^2$)   (Expression 25)

The engine inertia resistance coefficient is a sum of a coefficient of inertia resistance on the engine crankshaft and a coefficient of inertia resistance at the input side of the torque converter. On example of the engine inertia resistance coefficient is 0.011661 (kg·m·s$^2$).

The primary pulley inertia resistance power is obtained from Expression 26.

primary pulley inertia resistance power (kW/s)=primary pulley inertia resistance (N·m)×primary pulley revolutions (rpm)×2π/60 (s/min)/1000   (Expression 26)

The primary pulley inertia resistance is obtained from Expression 27.

primary pulley inertia resistance (N·m)=primary pulley rotational acceleration (rpm/s)×2π/60 (s/min)×primary pulley inertia resistance coefficient (kg·m·s$^2$)×9.8 (m/s$^2$)   (Expression 27)

The primary pulley inertia resistance coefficient is the sum of the coefficient of inertia resistance of the primary pulley, coefficient of inertia resistance at the output side of the torque converter, and coefficient of inertia resistance of the forward/reverse (FR) clutch. One example of the primary pulley inertia resistance is 0.0442 (kg·m·s$^2$).

The acceleration resistance power is obtained from Expression 28.

acceleration resistance power (kW/s)=vehicle weight (kg)×vehicle acceleration (m/s$^2$)×vehicle speed (km/h)×1000 (m/km)/60 (sec/min)/60 (sec)/1000(Expression 28)

The lower value of the vehicle acceleration is limited so that vehicle acceleration (m/s$^2$)≥−0.5 (m/s$^2$). The reason for this lower value limitation is to avoid adding the energy consumed by the brake pads to the amount of heat, since the vehicle acceleration is within −0.5 (m/s$^2$) when applying the brakes.

The air resistance power is obtained from Expression 29.

air resistance power (kW/s)=air resistance coefficient×air density (kg/m$^3$)×forward projected area (m$^2$)×(vehicle speed (km/h)×1000 (m/km)/60 (sec/min)/60 (sec))$^3$/1000   (Expression 29)

While the parameters differ for each type of vehicle and so forth, the following is one example.
Air resistance coefficient=0.306
Air density=1.293 (kg/m$^3$)
Forward projected area=2.29 m$^2$ The rolling resistance power is obtained from Expression 30.

rolling resistance power (kW/s)=rolling resistance coefficient×vehicle weight (kg)/9.8 (m/s$^2$)×vehicle speed (km/h)×1000 (m/km)/60 (min/h)/60 (sec/min)/1000   (Expression 30)

While the parameters differ for each type of vehicle and so forth, the following is one example.

Rolling resistance coefficient=0.04 (common paved road)

Vehicle weight=1,400 (kg)

According to the implementation described above, in a case where both the absolute value of change in estimated voltage of ATF temperature sensor when external air is hot and the absolute value of change in estimated voltage of ATF temperature sensor when external air is cold are no greater than 0.05 V/min, and the absolute value of change in voltage of the ATF temperature sensor is 0.025 V/min or greater, and this state continues for 60 seconds or longer, an output voltage stuck malfunction of the fluid temperature sensor 22 can be determined. Thus, suitable and accurate diagnosis can be performed.

According to the implementation, the following advantages can be obtained:

(1) An output voltage stuck malfunction of the temperature sensor is determined in a case where the amount of change of the output voltage estimation value calculated based on the operating state of the vehicle is equal to or above the first threshold value, while, the amount of change of output voltage of the temperature sensor is equal to or below a second threshold value. Accordingly an output voltage stuck malfunction may be suitably determined.

(2) Accuracy of determination may be improved by performing determination in accordance with the duration of a state in which the amount of change of the output voltage estimation value is equal to or above a first threshold value and the amount of change of output voltage of the temperature sensor is equal to or below a second threshold value, and this state continues for a predetermined amount of time or longer.

(3) Accuracy of determination may be improved by calculating the output voltage estimation value for each of a hot external air state and a cold external air state, and determining the output voltage stuck malfunction only in a case where the output voltage estimation value is equal to or above the first threshold value for both.

Modification

The present invention is not restricted to the above-described implementation; rather, various changes and modifications can be made, all of which are within the technical scope of the present invention.

For example, the temperature sensor according to the implementation has been described as being a fluid temperature sensor for a CVT which increases/reduces revolutions of an engine, but the present invention is not restricted to this arrangement. For example, the temperature sensor according to the present invention may be used for malfunction diagnosis of a fluid temperature sensor in any of a manual shift transmission (MT), geared automatic transmission (AT), dual clutch transmission (DCT), automated manual transmission (AMT), all-wheel-drive (AVSD) transfer case, and differential.

Moreover, the driving power source is not restricted to an engine, and may be an electric motor, or may be a hybrid system combining an engine with an electric motor.

The invention claimed is:

1. A diagnosis device for a temperature sensor provided to a power transmission device that transmits driving force generated by a driving power source of a vehicle, the diagnosis device comprising:

an output voltage estimating unit to calculate an output voltage estimation value of the temperature sensor, based on the operating state of the vehicle; and an output voltage stuck malfunction determining unit to determine an output voltage stuck malfunction of the temperature sensor, in a case where the amount of change of the output voltage estimation value is equal to or above a first threshold value, and the amount of change of output voltage of the temperature sensor is equal to or below a second threshold value.

2. The diagnosis device for a temperature sensor according to claim 1, wherein the output voltage stuck malfunction determining unit determines the output voltage stuck malfunction, in a case where the amount of change of the output voltage estimation value is equal to or above a first threshold value and the amount of change of output voltage of the temperature sensor is equal to or below a second threshold value, and this state continues for a predetermined amount of time or longer.

3. The diagnosis device for a temperature sensor according to claim 1, wherein the output voltage estimating unit calculates an output voltage estimation value for each of a first external air state and a second external air state, the first external air state having a higher temperature than the second external air state;

and wherein the output voltage stuck malfunction determining unit determines the output voltage stuck malfunction only in a case where the output voltage estimation value is equal to or above the first threshold value in both the first external air state and the second external air state.

4. The diagnosis device for a temperature sensor according to claim 2, wherein the output voltage estimating unit calculates an output voltage estimation value for each of a first external air state and a second external air state, the first external air state having a higher temperature than the second external air state;

and wherein the output voltage stuck malfunction determining unit determines the output voltage stuck malfunction only in a case where the output voltage estimation value is equal to or above the first threshold value in both the first external air state and the second external air state.

5. The diagnosis device for a temperature sensor according to claim 1, wherein, a different sensor than the temperature sensor is malfunctioning if the amount of change of the output voltage estimation value is greater than the second threshold value.

6. The diagnosis device for a temperature sensor according to claim 1, wherein the output voltage stuck malfunction determining unit determines the output voltage stuck malfunction, in a case where the amount of change of the output voltage estimation value is above a first threshold value and the amount of change of output voltage of the temperature sensor is below a second threshold value, and this state continues for a predetermined amount of time.

* * * * *